United States Patent [19]

Pedigo et al.

[11] Patent Number: 4,769,881
[45] Date of Patent: Sep. 13, 1988

[54] HIGH PRECISION TENS APPARATUS AND METHOD OF USE

[76] Inventors: Irby R. Pedigo, 7750 McCreary Rd., Seven Hills, Ohio 44131; Steven G. Belovich, 18872 Meadow La., Strongsville, Ohio 44136

[21] Appl. No.: 904,017

[22] Filed: Sep. 2, 1986

[51] Int. Cl.⁴ .............................................. A61N 1/00
[52] U.S. Cl. .................................. 128/419 R; 128/421
[58] Field of Search ........... 128/421, 422, 741, 419 R, 128/419 C, 420 A

[56] References Cited

U.S. PATENT DOCUMENTS

| | | | |
|---|---|---|---|
| Re. 32,091 | 1/1986 | Stanton | 128/421 |
| 2,700,975 | 2/1955 | Hopfinger et al. | 128/421 |
| 3,294,092 | 12/1966 | Landauer | 128/421 |
| 3,645,267 | 3/1972 | Hagfors | 128/421 |
| 3,894,532 | 7/1975 | Morey | 128/421 |
| 3,983,881 | 10/1976 | Wickham | 128/421 |
| 4,016,870 | 3/1977 | Lock | 128/421 |
| 4,088,141 | 5/1978 | Niemi | 128/421 |
| 4,092,986 | 6/1978 | Schneiderman | 128/421 |
| 4,102,347 | 7/1978 | Yuki | 128/421 |
| 4,210,151 | 7/1980 | Keller, Jr. | 128/421 |
| 4,233,986 | 11/1980 | Tannenbaum | 128/421 |
| 4,237,899 | 12/1980 | Hagfors et al. | 128/421 |
| 4,255,790 | 3/1981 | Hondeghem | 128/421 |
| 4,372,319 | 2/1983 | Ichinomiya et al. | 128/421 |
| 4,408,617 | 10/1983 | Auguste | 128/421 |
| 4,520,825 | 6/1985 | Thompson et al. | 128/421 |
| 4,528,984 | 7/1985 | Morawetz et al. | 128/421 |
| 4,580,570 | 4/1986 | Sarrell et al. | 128/421 |
| 4,582,063 | 4/1986 | Mickiewicz et al. | 128/421 |
| 4,598,713 | 7/1986 | Hansjurgens et al. | 128/421 |
| 4,669,477 | 6/1987 | Ober | 128/421 |

Primary Examiner—Kyle L. Howell
Assistant Examiner—George Manuel
Attorney, Agent, or Firm—Oblon, Fisher, Spivak, McClelland & Maier

[57] ABSTRACT

A transcutaneous electrical nerve-stimulation therapy apparatus and method having absolute protection for the patient from shock and automatic operation. The apparatus may operate in three modes, either controlled by timer, operating continuously or put in an automatic mode where the timer is automatically reset when the probe is removed from the patient and then recontacted. A circuit is provided for checking the continuity between the patient and the probes before each and every stimulation pulse. These pulses are generated at the same frequency and with a constant phase shift from the stimulation pulses. At the start of each set of stimulation pulses, the pulses are slowly ramped up over a 4–5 second interval so as to prevent any initial jolt to the patient. The device may also be used to locate appropriate application points on the patient's body. The pulses applied are variable current pulses having a fixed voltage.

23 Claims, 5 Drawing Sheets

HIGH PRECISION TENS APPARATUS AND METHOD OF USE

BACKGROUND OF THE INVENTION

1. Field of the Invention

This invention relates generally to a transcutaneous electrical nerve stimulation (TENS) apparatus and more particularly to a TENS therapy apparatus and method having safety features and automatic operation.

2. Discussion of the Background

Various kinds of transcutaneous electrical stimulation of tissues have been utilized, especially in the last twenty years, for a variety of medical treatments. In particular, the stimulation has been used in order to treat various kinds of pain associated with various kinds of medical conditions and injuries to stimulate muscles, to reduce swelling and inflammation and for various other medical treatments.

The prior art includes many devices which have specialized features for protecting the patient, making the device easier to use and improving the results of the procedure. While these improvements have made the treatment of patients more safe, more effective and more comfortable, there remain many problems and areas for improvement for each device.

In U.S. Pat. No. 4,233,986, an apparatus and method is shown for a transcutaneous electrical stimulation treatment for pain. The apparatus includes a pulse generator and skin electrodes for applying the pulses. The width of the pulses may be varied. The electrodes also include a method for finding nerves in the patient's skin.

Another related device shown in U.S. Pat. No. 4,088,141 describes a fault control circuit for use with an electrical stimulator used on a patient. The device is disabled when the electrode impedance exceeds the threshold level or when the output current level undergoes a large change.

Another use of this type of apparatus is found in U.S. Pat. No. 4,016,870 which is used to locate acupuncture points on the skin. While this device locates the desired points, it does not involve actual electrical stimulation.

Another therapeutic apparatus is shown in U.S. Pat. No. 4,580,570. This apparatus discloses different modes of operation so that current may be either continuously applied or periodically interrupted.

Other electrical stimulation devices are shown in other U.S. patents such as U.S. Pat. Nos. 4,598,713, Re. 32,091, 3,645,267, 3,894,532 and 3,983,881.

These devices generally have the same basic function of applying electrical stimulation to the patient through some form of probes. Some of these devices contain safety features so that the patient is not subjected to a sudden shock and so that the device may be shut off if the probe is not in good contact. Other devices show various methods of controlling the various parameters associated with the electrical pulses. Some of the other devices have various forms of controls for making the application of the pulses more comfortable and effective for the patient.

Although these devices and their methods of operation have provided great relief of pain for the patient and have been reasonably effective in their application, several problems still remain in their use. The use of these devices is still not completely safe and comfortable for the patient in many cases. If the probe does not remain in good contact with the patient's skin, it is often possible to have a sudden increase in the voltage applied to the body. This results in a sudden jolt to the patient which is most uncomfortable. Also, many patients find that the sudden application of the high voltage pulses at the beginning of the treatment is similarly uncomfortable. Accordingly, there is definite room for improvement in order make the patients more comfortable.

Operators also find the application of these devices to be somewhat inconvenient at various times. It is difficult to control the placement of the probe on a particular place on the body while having to constantly readjust the various dials and to monitor the various displays on the device. This may lead to discomfort for the patient if the operator's attention is diverted to adjust the dials and the probe is either moved or loses contact with the skin. The necessity to constantly reset the dials is also a problem for the operator. Most of the devices also do not include all the features shown in the different patents listed above and while some of the devices may have some form of some features, none of the devices contain all of the features indicated.

SUMMARY OF THE INVENTION

Accordingly, an object of this invention is to provide a new and improved TENS therapy apparatus and method which is safe and convenient to use.

Another object of this invention is to provide a TENS apparatus and method which provides a constant check on the continuity between the patient and the probe in order to protect against discomfort to the patient.

A further object of this invention is to provide a TENS apparatus and method which locates the appropriate application points.

A still further object of this invention is to provide a TENS apparatus and method which may operate in three different modes including an automatic operation mode to relieve the operator of the need to constantly monitor the apparatus.

Another object of this invention is to provide a TENS apparatus and method utilizing variable current pulses with a fixed voltage.

Another object of this invention is to provide a TENS apparatus and method which has a programmed gradual increase of the voltage to reduce the shock effect to the patient.

Briefly, these and other objects of the invention are achieved by providing test pulses between each and every stimulation pulse to check for the continuity between the probe and the patient. Other objects are also achieved by providing three modes of operation including an automatic mode which resets the settings on the device. In order to provide a more comfortable application to the patient, a slow build-up of voltage is first applied to the patient in order to prevent an uncomfortable sudden jolt. Variable current pulses are also utilized to provide a mor effective treatment.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
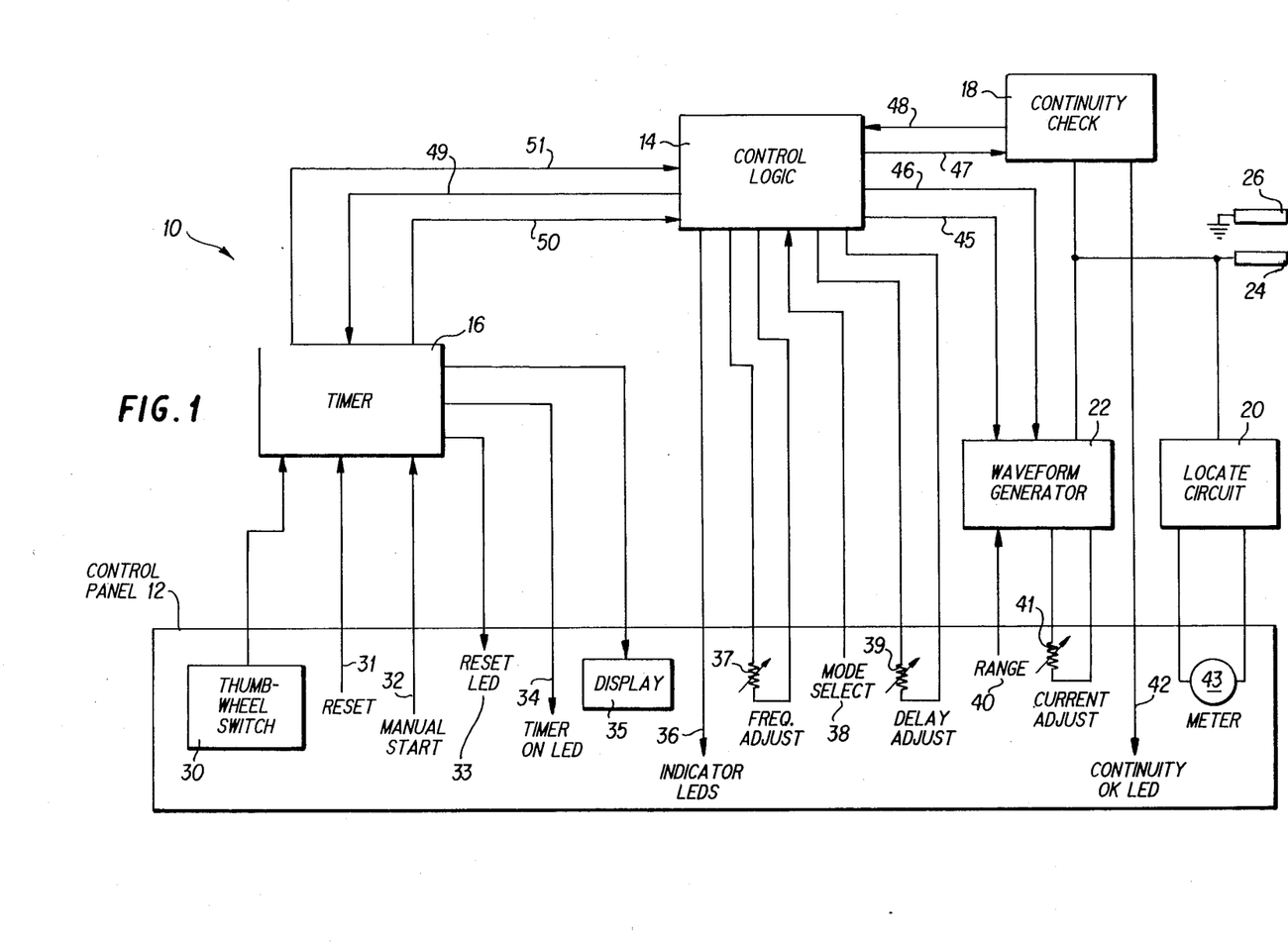
FIG. 1 is a block diagram of the present invention.

Various other objects, features and attendant advantages of the present invention will be more fully appreciated as the same becomes better understood from the following detailed description when considered in connection with the accompanying drawings in which like reference characters designate like or corresponding parts throughout the several views and wherein the present invention is generally indicated by reference numeral 10 in FIG. 1. The apparatus includes a number of circuits 14 through 22, two probes 24 and 26 and a control panel 12. The panel includes a number of adjustable switches to control the various functionings of the apparatus. It also includes displays and indicators for informing the operator as to the functioning of the apparatus.

The most important circuit to the apparatus is the control logic section 14. The circuit is responsible for the proper synchronization of all the other sections and for the receipt of control signals from the panel. This circuit determines the requested function of the operator and controls the other sections in order to produce the desired result.

The timer circuit 16 may be set by the operator to determine the duration of the treatment from 1 to 99 seconds utilizing the thumbwheel switch on the control panel. The timer determines when the preselected time interval has expired and indicates to the control logic when this has happened. The timer also controls a display to indicate to the operator the selected duration and the time remaining in the treatment.

The wave form generator 22 forms the electrical pulses to be applied to the probe. Under the control of the control logic circuit, the wave form generator produces electrical pulses of the desired size which ar applied to probe 24. The size of the pulse is determined by the range select switch and the current adjustment switch in the control panel. The range select switch acts as a rough adjustment by selecting the general size of the pulses. The current adjustment acts as a fine control to select the exact size of the pulse required.

The continuity check circuit 18 acts to protect the patient by assuring that contact between the patient and the probe is maintained at all times. A check is made between each and every stimulation pulse to determine the resistance between the two probes through the patient. This resistance is compared to a reference level to determine whether the resistance is of a proper size. If the resistance is too large, the continuity check circuit indicates to the control logic circuit that the probe is out of contact. The control logic circuit then immediately shuts down the apparatus until the probe is properly placed.

The locate circuit 20 is used to find the proper application point of the probe. The circuit determines when a high capacitance exists between the two probes. The result of this measurement is then displayed on the meter in the control panel.

Two probes are provided with the apparatus. Probe 24 is connected to the continuity check circuit, the wave form generator circuit and the locate circuit. The other probe 26 is connected to ground at all times. The two probes may be moved about the patient's body to the particular location required for the treatment or to locate such a location. The simulation pulses are applied to probe 24 from the wave form generator. The pulses then travel through the patient's body and the other probe to ground.

The machine has three distinct operating modes. The first mode is a "one shot" mode where the machine generates stimulation pulses for a fixed time interval as set by the thumbwheel switch on the control panel. This time interval is initiated by depressing the manual start button on the control panel. The second mode or "continuous" mode permits the generation of stimulation pulses continuously, rather than being limited by a timer setting. In this mode, the treatment continues until the operator manually stops the treatment by removal of either or both the probes from contact with the patient. Resumption of the treatment is accomplished by re-touching the patient with both probes. The third mode or "auto restart" mode is similar to the first mode except that the timer is automatically restarted upon the detection of the reestablishment of continuity between the probes and patient. Thus, when the timer expires, a simple removal and replacement of the probes on the patient is sufficient to restart the timer, rather than requiring the settings to be reset. Thus, in this mode it is not necessary to readjust any control panel switches. This allows the operator to concentrate on the location of the probe and the condition of the patient. Thus, once the initial settings have been determined the operator can continue to apply treatments to the patient in various locations without ever having to make any adjustments to the device.

In any of these modes, the machine accurately locates and provides therapeutic electrical stimulation to neuro-electric points in the body, some of which may be referred to as acupuncture points. In using this apparatus, there is no discomfort to the patient. When the electrodes are both in contact with the patient's skin, the machine can automatically be turned on to locate an appropriate point for application. This may immediately be followed by a gradual build-up of power to the normal preset level. Electrodes may also be moved to massage the skin with electrical stimulation over a large inflamed area or along inflamed tendons without any discomfort to the patient. When either of the electrodes are removed from skin contact, the machine automatically shuts down. It will also automatically start up and repeat the locate and stimulate sequence without the necessity for touching any controls. With the proper positioning of the electrodes, the machine dramatically improves the range of motion in the joints of patients treated for pain in this area. It was observed while treating a painful condition that the inflammation and swelling at the site of an injury or inflamed area was reduced. Another observation concerned the reduction in time required for soft tissue healing after treatment.

These effects are produced by varying the pulse frequency and the current of the applied electrical pulses.

This is different from most prior art devices which utilize a voltage control. In addition, the pulses of the present invention are asymmetrical and have a constant voltage amplitude.

In operating the device, the patient's safety and comfort is very important. Accordingly, in order to avoid any possibility of electrical shock or other unpleasant sensation, the present TENS therapy apparatus is given a certain amount of intelligence in order to perform various internal tests and checking procedures while producing the stimulating pulses. In particular, the machine will not allow the generation of stimulating pulses until it is ascertained that the electrodes are in proper contact with the patient's skin. The machine also causes the intensity of the stimulating pulses to be slowly increased to the level selected so as to avoid any initial jolt to the patient. Provision is made for a timing device with a display for accurately controlling the duration of the therapy.

As explained above, the control logic circuit is responsible for the proper synchronization of all the other sections. The control logic receives an input from the mode select switch 38 to indicate to the control logic which of the three operating modes is desired. It also receives a signal from the delay adjustment 39 to indicate how much delay time is desired before bringing the stimulation pulses to full strength. The control logic also receives an indication from the frequency adjust circuit 37 to indicate the desired pulse frequency. The control logic forwards to the control panel a number of signals indicating the condition of the device which are displayed by a number of LEDs 36.

The control logic circuit also sends two signals to the waveform generator. Signal 45 is a waveform generator clock signal which indicates to the waveform generator when the stimulation pulses should occur. Signal 46 is a slow start ramp signal which indicates to the waveform generator that the pulses are to be increased in intensity until the full strength is reached. The full intensity of the pulses are determined by range select switch 40 and current adjustment 41.

The control logic also produces a continuity clock signal 47 which is received by the continuity check circuit. This circuit indicates the proper time for the continuity check circuit to measure the continuity between the probes and the patient. The continuity check circuit returns the results of this measurement through the continuity OK output signal 48.

An indication 42 that the continuity is OK is displayed on the control panel. Control logic also produces an automatic timer start signal 49 which is sent to the timer. This signal is used to control the timer when the device is in the automatic mode. The timer also forwards to the control logic a timer on signal 50 which indicates to the control logic circuit when the timer is operating and when the preset time has expired.

The timer 16 receives an indication of the requested duration of the treatment from thumbwheel switches 30. A manual reset button 31 and a manual start button 32 are also provided to give the operator manual control over the timer. The timer produces a signal 33 to indicate that the timer has been reset. It also produces a display 34 indicating that the timer is on. This signal is a visual indication that the timer on signal 50 is present. The timer also produces a display 35 for indicating the duration of treatment which it has received. When the device is in one of the two modes governed by the timer, the display will be decremented to indicate the time remaining for treatment.

Figure 2:
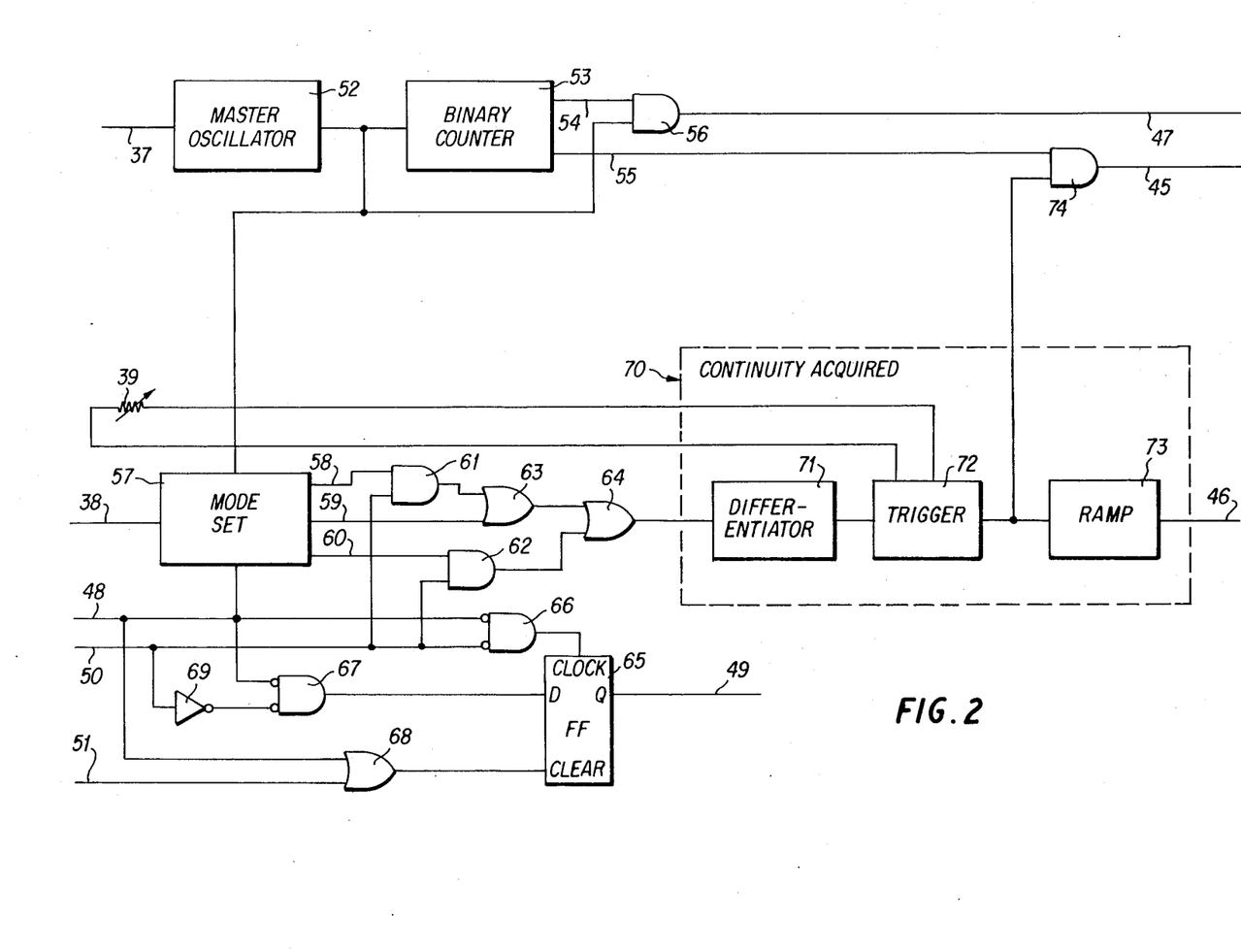
FIG. 2 is a schematic diagram of the control logic circuit of FIG. 1.

Turning now to FIG. 2, a more detailed description of the control logic is seen therein. The various inputs to the control logic are shown at the left hand side indicated by the same reference numerals as in FIG. 1. Master oscillator 52 is controlled by the frequency adjustment 37 to produce the pulse frequency as requested by the operator. The output pulses from the oscillator are fed to the binary counter 53 which sequentially counts the pulses. It is well known with such counters that the output signals are produced which have fixed frequency relationships with each other, differing by multiples of 2. Thus, outputs 54 and 55 may be selected so that they differ in frequency by a factor of 2. These outputs may be logically combined to produce periodic signals that have fixed phase relationships with each other. By doing this, the continuity clock pulses and waveform generator clock pulses may be controlled to be out of phase with each other so that the continuity checks do not interfere with the stimulation pulses. Output 54 is combined in an AND gate 56 with the output from the master oscillator in order to produce continuity clock pulses 47 which are of a size equal to one pulse from the master oscillator.

As explained above, the present device has the potential for operating in three different modes. The particular mode selected is determined by switch 38 which is connected to a mode set circuit 57. This circuit also receives timing pulses from the master oscillator and control pulses from the continuity OK input 48. This circuit may take a number of forms and in particular may be three flip flops each of which corresponds to one selection of switch 38. The flip flop would then be clocked by the pulses from the master oscillator to produce an output which is gated by the continuity OK signal. In order for any waveform generator pulses to be produced, a signal must be present on the continuity OK input 48. Depending on which mode is selected, an output is provided on one of the three outputs of the mode set circuit. Output 58 indicates that the device is in the one-shot mode. Output 59 indicates that the device is in the continuous mode. Output 60 indicates that the device is in the auto restart mode. Outputs 58 and 60 are gated through AND gates 61 and 62 respectively. The other input to these AND gates is connected to the timer on input 50. By requiring this input, no pulses may be passed in these modes unless the timer is operable. Thus, the actuating pulses from the timer on input are removed when the timer has expired. Output 59, indicating a continuous mode does not require this pulse since it may operate without regard to the timer. Gate 61 and output 59 are connected in an OR circuit 63 which passes either signal when the device is in one of those two modes. The output of this OR circuit is itself logically ORed with the output of the AND gate 62 by OR gate 64. Thus, an output is provided from OR gate 64 when the device is in any of the three modes and the proper combination of timing and continuity signals is also present.

Flip flop 65 is used to produce an automatic timer start signal 49, which controls the timer circuit 16. This signal is utilized to automatically start the timing cycle for the duration of the treatment. The flip flop is connected to the timer on input 48, the continuity input 50 and the reset input 51. These inputs are connected to the flip flop through gates 66–69. These gates control the flip flop to produce an automatic start signal only when the continuity OK signal is present and when the timer on signal has stopped. Thus, when the timer is on, the automatic start signal is removed. It is only when the timer on signal has stopped that the automatic start signal may be activated on resumption of continuity. Thus, the input to the AND gate 67 includes inverter 69 to obtain the logical inverse of the input that is received by AND gate 66. Gate 68 also receives the reset pulse from timer 16 which is generated when power is initially applied to the device. This serves to prevent false triggering of the timer due to momentary indeterminate signal states during power up.

In order for the device to produce a ramp up signal when the probe is first applied to the patient, it is necessary to first establish when continuity is acquired. This is accomplished using the continuity acquired circuit 70. This circuit receives the output of OR gate 64 which indicates when the device is set to one of the modes and the proper conditions are present. One of these required conditions is alway the continuity between the patient and the probe. Thus, when the conditions are present, the output from OR gate 64 will change state. This change is detected in the continuity acquired circuit using a differentiator circuit 71. This device, which may include a capacitor and resistor differentiator network, determines when the output from OR gate 64 suddenly changes level. When this happens, the output from differentiator 71 causes trigger circuit 72 to produce an output signal. The duration of this output signal serves to provide a specific delay in the application of full force stimulation signals. The amount of delay is set by the delay adjustment 39. The termination of this presettable delay controls a ramp circuit 73 which may include a capacitor or similar device for causing the output signal 46 to ramp up to a set level, to slowly increase the amptitude of the stimulation pulses. The output of trigger circuit 72 is also used to gate clock pulses from output 55 of the binary counter to form the waveform generator clock signals 45. Since the presence of the gating signal from trigger circuit 72 is dependent on the proper conditions being satisfied in the mode set circuit and intervening gate circuits, waveform generator pulses may not occur until all required conditions are met. Thus, the waveform generator pulses may not occur unless the continuity OK signal is present and in those modes that require it, the timer on signal is present.

It is easily seen then that the continuity clock pulses 47 and the waveform generator clock pulses 45 are out of phase with each other due to the particular outputs of the binary counter selected. It should be noted that even if the frequency of the master oscillator is changed, the phase difference between these two clock pulses will always remain the same regardless of the frequency. This is extremely important since it is necessary that the continuity be checked each and every time before a stimulation pulse is applied. Since both of the clock pulses are generated by the same counter circuit, these two signals will always have the same frequency and always be out of phase by the same amount. Thus, it is impossible to form a stimulation pulse without first producing a continuity check signal each and every time. Also, the circuit requires that the continuity OK signal be received before the gating signal can be produced which passes the waveform generator signal.

It should also be noted that the gating signal is produced only when the device requires the waveform generator clock signals. Thus, this prevents the device from operating when not necessary and thus conserving power.

It also should be noted that the mode set circuit 57 samples the position of the mode select switch 38 at the same frequency as supplied to the binary counter. Thus, this ascertains that the mode has not been changed by the operator since the last pulse.

Although not shown in the figure, various indicator LEDS are possible to indicate the proper functioning of the control logic and to indicate to the operator important information concerning the device. Thus, three separate indicators could be actuated by the mode set circuit to inform the operator as to which mode the device was operating in. Likewise, an indication could be produced by the continuity acquired circuit to indicate that the ramping procedure was in effect. Another indicator could inform the operator that the gating signal was present to enable the waveform clock. Some of the other indicators could be connected to the various points of the control logic in order to inform the operator as to the proper functioning of the control logic.

Figure 3:
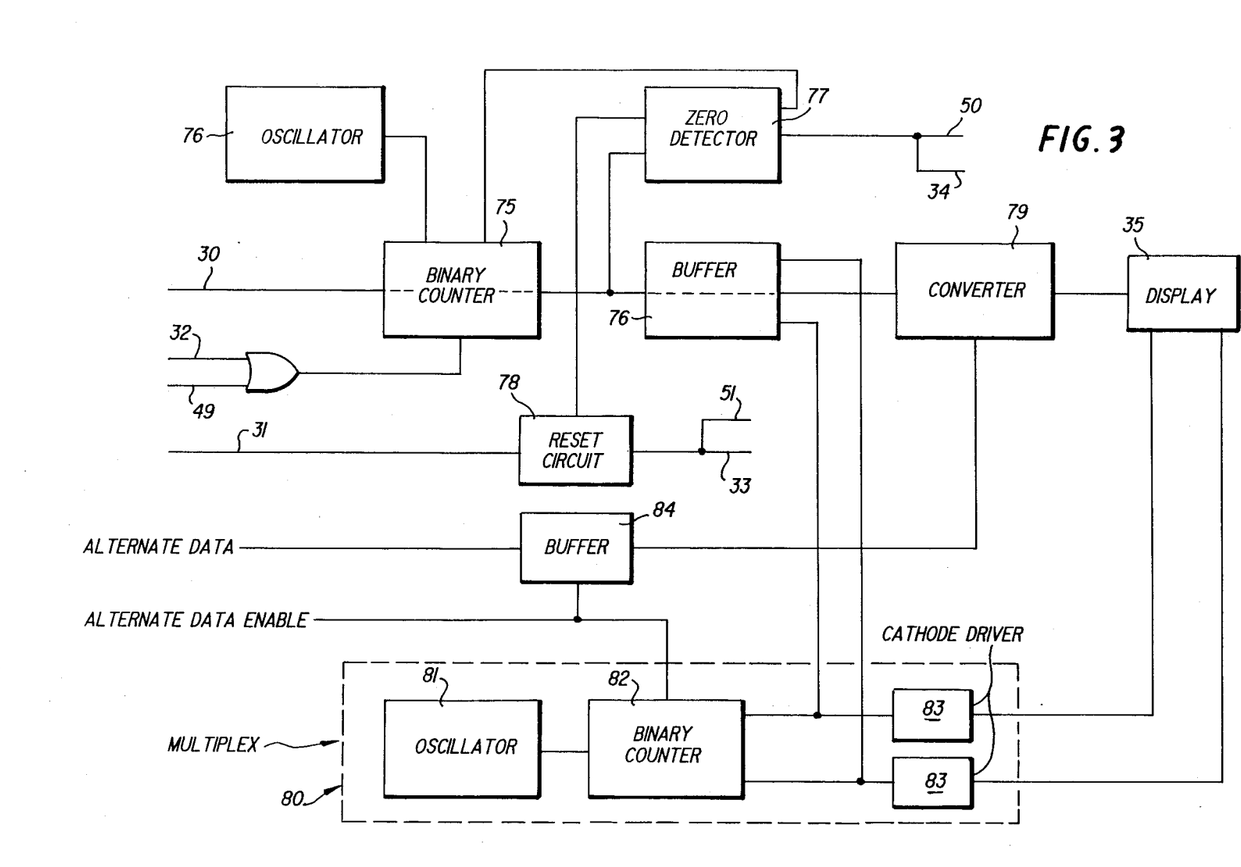
FIG. 3 is a schematic diagram of the timer circuit of FIG. 1.

Turning to FIG. 3, the specific circuitry of the timer 16 is seen therein. As was indicated above, the thumbwheel switch 30 is used to set into the timer the duration of the treatment desired. Depending on the apparatus used, any number of digits could be utilized in this switch. However, in the present embodiment the duration may last from 1 to 99 seconds and accordingly the thumbwheel switch has two digits. The setting of these switches is sent to a binary counter 75. Although only a single line is indicated in the drawing actually a line for each binary bit is required from the switches. In order to set the digits into the binary counter, it is possible to include a resistor network (not shown) between a positive power source and the input lines from the switches. The binary counter is also connected to a oscillator unit 76 which is set at a frequency of 1 Hz. This oscillator produces one second pulses in order to count the binary counter down to 0 indicating the end of the duration of the treatment. The binary counter is also connected to a buffer which stores the present value of the counter. A zero detect circuit 77 is connected to the output of the binary counter in order to determine when the counter reaches 0. When a 0 is detected, the binary counter is then reset in order to be ready for the next stimulation interval. The zero detect circuit also produces an output 50 which indicates to the control logic that the timer is operative and that the duration has not yet expired. This signal is also used to drive the timer on display indicator 34 on the control panel. The manual reset button 31 on the control panel can be used to trigger a reset circuit 78 which is always automatically triggered upon power up. This reset circuit also triggers the zero detect circuit in order to reset the binary counter. The reset circuit also produces a reset signal 51 which is fed to the control logic circuit as explained above. A reset indicator 33 may also be controlled from this output.

Converter 79 receives the binary information from the buffer 76 relating to the number in the counter. The converter changes this binary information into a seven segment code for driving a seven segment indicator in the display 35. Since two digits are held in the buffer 76, it is either necessary to have a converter which is capable of handling two digits or to have a multiplexing circuit in order to alternately display the two digits. In order to reduce unnecessary wiring between the converter 79 and the display 35, the multiplexer concept is preferred.

Multiplexing circuit 80 is provided to alternately enable the two halves of the buffer 76 and at the same time to alternately control the cathodes of the display. Thus, the multiplexing circuit contains an oscillator 81 which drives a binary counter 82 to produce signals that are out of phase with each other. The two signals from counter 82 are used to alternately gate the signals from the buffer 76 to the converter 79. At the same time, these two signals also actuate the two cathode drivers 83 alternately. The switching time in the display may be made quick enough that the display appears continuous to the human eye. It is also possible to utilize a similar arrangement when more than two digits are utilized by obtaining additional outputs from the binary counter which are out of phase with each other and driving the additional cathodes at the same phase.

It is also possible to display additional information, if desired, through the display device 35. Thus, provision is made in the timer circuit to receive some form of alternate data, such as voltage signals or other important data, which may be internal or externally applied, and which is held in buffer 84. This information may contain as many digits as may be displayed in a display 35. An enabling pulse for the alternate data may be applied to the buffer to indicate that this data is to be transferred into the converter 79. At the same time, the enable pulse is applied to the multiplexing circuit in order to prevent signals from being applied to the buffer circuit 76 and thus preven transfer of this information. This blocking may be accomplished using appropriate gating which is not shown in the drawings.

Figure 4:
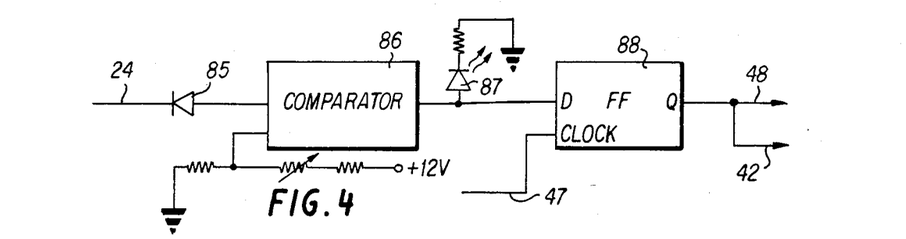
FIG. 4 is a schematic of the continuity check circuit of FIG. 1.

Turning now to FIG. 4, a schematic diagram of the continuity check circuit is presented therein. The continuity check circuit is connected to probe 24 which is applied to the patient. This device ascertains that there is continuity between the patient probe 24 and probe 26 which is grounded. This is done by examining the resistance between the probe 24 and ground during the period indicated by the continuity clock signal 47.

Comparator 86 compares the current which is drawn through diode 85 and hence to the probes and patient with a set reference level. The comparator may include an operational amplifier to perform this comparison. When the current is at the proper level indicating that the patient is in proper contact with the two probes, an output is produced by the comparator. The output of the comparator passes through a light emitting diode 87 which is not present on the control panel. However, it is possible for the operator to see the flashing of the device through the casing of the apparatus when diagnostic testing is required. The signal passing through the diode 87 is clocked into flip flop 88 utilizing the continuity clock signal 47 produced by the control logic circuit. When this signal is present at the time that the clock signal is present, the continuity check circuit sends a continuity OK signal 48 back to the control logic circuit. At the same time, the indicator LED 42 on the control panel is likewise activated.

Figure 5:
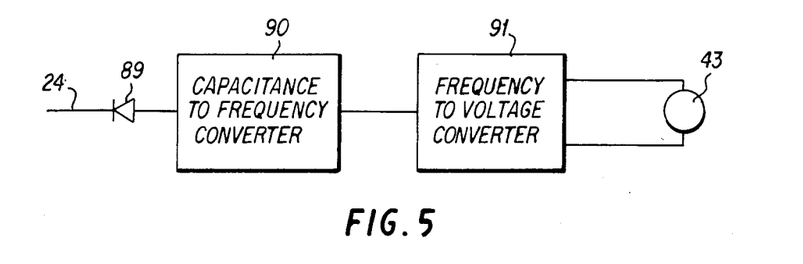
FIG. 5 is a schematic diagram of the locate circuit of FIG. 1.

Turning now to FIG. 5, the circuitry of the locate circuit is presented therein. This circuit allows for the probe to be moved across the skin of the patient in order to locate the points at which stimulation pulses should be applied. This is done by noting locations of high capacitance between the two probes. The capacitance to frequency converter 90 is connected to probe 24 through a diode 89. This converter may include any circuitry which converts such capacitance to a frequency signal. However, preferably it includes an oscillator which is connected to an RC network. By making the size of the capacitor of the order typically seen by the probes, changes in the capacitance of the probes will change the time constant of the RC network and accordingly the frequency of the oscillator. Thus, the frequency of the output signals of converter 90 is determined by the capacitance between the two probes. This frequency signal is then fed to a frequency to voltage converter 91 to produce an output which is indicative of the voltage. This circuit may include any such converter but preferably is a filter network made of operational amplifiers. The output from this converter is then fed to a voltmeter which has a display that is mounted on the control panel. By watching the display 43 of the meter, the operator may move the probe along the patient's body until the display indicates the point of maximum capacitance. Such points are considered proper stimulation points for the apparatus. It is also possible to utilize an ammeter rather than a volt meter if desired.

Figure 6:
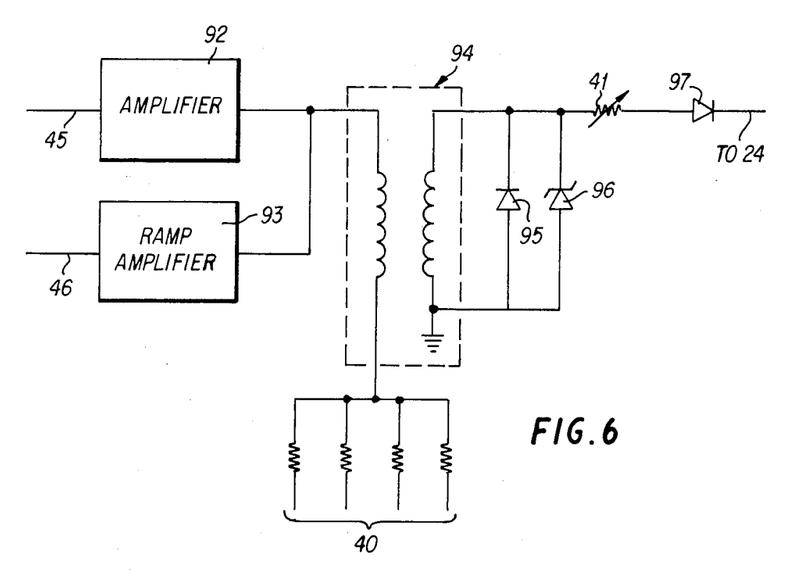
FIG. 6 is a schematic diagram of the waveform generator of FIG. 1.

Turning now to FIG. 6, the waveform generator is shown including two input signals from the control logic circuit. Waveform generator clock signal 45 is applied to an amplifier 92 which amplifies the signal by a large amount. Since the input clock signal is a square pulse wave, the output signals from the amplifier are on/off pulses. This output signal is applied to the primary winding of transformer 94. At the same time, signal 46 which is the slow start ramp signal from the control logic circuit passes through a ramp amplifier 93 which also increases its signal. The output of this amplifier is likewise connected to the input of the primary winding of the transformer 94. This signal acts to ramp the output signal to the full desired power of the stimulation pulses over a short time interval of four or five seconds to prevent discomfort to the patient.

The other end of the primary winding of the transformer is connected to power select switch 40 which is included in the control panel. This switch acts to select different ranges of power desired by the operator. Each of four ranges is shown as having a resistance of different value. By selecting one of the different resistances, the amount of power passing through the transformer windings is controlled.

The secondary winding in the transformer generates a signal based on the signal produced in the primary winding, as is well-known. The signal is isolated from the device by the transformer to protect the patient from shock. This signal is rendered unipolar by diode 95 and its voltage is limited by Zener diode 96 to 200 volts. The resultant signal passes through current adjustment 41 to control the amount of current passing through diode 97 to the probe 24. It should be noted that range switch 40 produces a course adjustment to the strength of the signal produced in the probe while the current adjustment produces a finer adjustment. The Zener diode 96 causes the voltage of the pulse to be held at a constant 200 volts, once the initial period is passed. However, it is possible for the operator to adjust the strength of the current utilizing current adjustment 41. By applying pulses to the patient which have a constant voltage and a variable current, Applicants have produced more effective therapeutic treatment. These pulses differ from those of the prior art devices where a variable voltage signal is provided.

Figure 7:
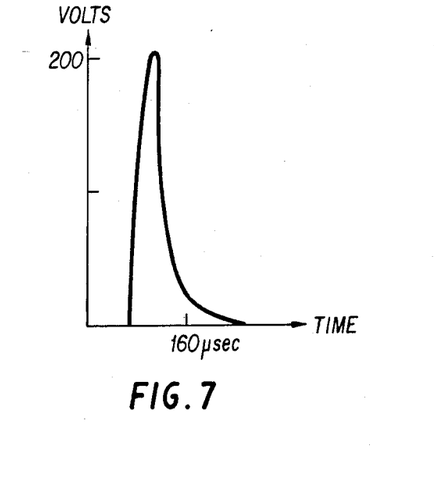
FIG. 7 is a graph showing the waveform of the pulses of the present invention.

Turning now to FIG. 7, this figure indicates the shape of the stimulation waveform. As seen in the figure, the full-height of the pulse is 200 volts with a sharp rising edge and a less sharp trailing edge. The peak width of the pulse is roughly 15 micro seconds wide while the pulse is roughly 160 micro seconds wide at the 15–20 volt level.

Figure 8:
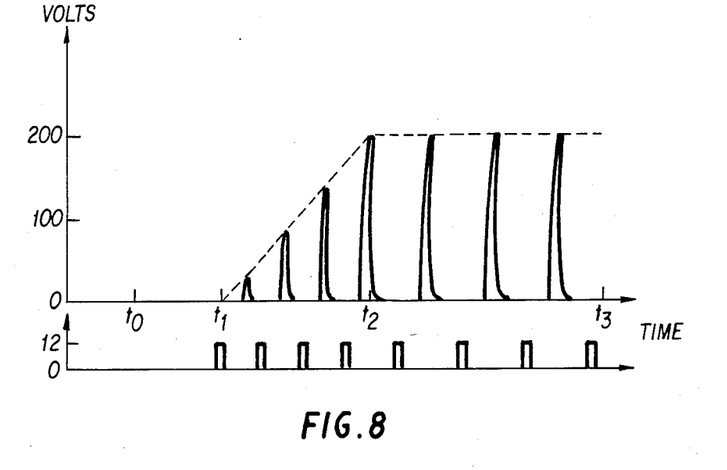
FIG. 8 is a timing diagram showing the relationship between the various timing pulses of the device.

FIG. 8 shows the timing diagram indicating the relative times and heights of the various waveforms of the present device. At time $t_0$ the probes are brought into contact with the patient. At this time no stimulation pulses are yet applied. This may be due to the lack of proper continuity between the patient and the probes. It also may be caused by a built-in delay before the start of the application in order to give the operator a few seconds to properly locate the probe. The pulses then begin at time $t_1$ with a relatively small stimulation pulse. During the time period from $t_1$ to $t_2$ which is typically of the order of 4–5 seconds, the pulses produced follow a ramp signal indicated by the dotted line. At time $t_2$, the full ramp height is reached and the stimulation signals then reach a full peak amplitude of 200 volts. The pulses continue in a regular form until the time $t_3$ is reached which indicates the expiration of the duration of the treatment as indicated by the timer.

The lower line of the figure indicates the occurrence of the continuity check clock signals. Each of these signals is a square wave pulse having a height of 12 volts. Each of these pulses occur before a stimulation pulse and essentially halfway between these pulses. The continuity check pulses actually continue whether stimulation pulses are started or not although the extraneous pulses have been left out of this figure.

Thus, by utilizing the continuity check circuitry, the present device is given a certain degree of intelligence in the form of various internal tests and checking procedures in order to avoid discomfort to the patient. In particular, the machine will not allow the generation of stimulation pulses until it is ascertained that the electrodes are in proper contact with the patient's skin. Also, as described above, the machine causes the intensity of the pulses to be slowly increased to the level selected by the operator so as to avoid any initial jolt which would be uncomfortable for the patient.

As explained previously, a delay mechanism may initiate the application of the stimulation current after the desired probe location has been found, thus removing the necessity to readjust the controls of the device as is required in other machines of this type.

The power utilized for searching and locating a neuro-electric point is different from that needed for the treatment pulses. The machine is programmed to use a voltage level of 12 volts while searching. Once the search time has expired, the machine automatically increases the intensity of the pulses to permit treatment to take effect immediately. A delay of 5 seconds is incorporated so that the pulses reach the maximum intensity of 200 volts, thereby allowing additional time during which the probe may be positioned more firmly.

The therapy provided by the use of this machine has a cumulative effect, thus obviating the need for the patient to use a small portable device or to have electrodes implanted for use in post-operative pain control. When therapy has provided enough electrical nerve stimulation to increase the pain threshold, pain, including post-operative pain, will cease. By electrically stimulating the area of injury, of a chronic painful condition or of specific points in the nervous system enough, these will in turn stimulate the body's own pain killers into activity so that pain is controlled and eliminated thereby significantly reducing the need for narcotics while accelerating the healing process.

Some areas in which the present apparatus and method have been effective include:

1. Promoting healing of bone fractures by stimulating the surrounding tissues.

2. Promoting healing with pain relief of tendonites and tendon fractures by stimulating the tendon area.

3. Releasing muscle spasms and relieving muscle strain by appropriate placement of the electrodes during treatment.

4. Relieving or preventing atrophy of muscles and tendons caused by injury.

5. Relieving the pain associated with infections such as sinus infections, virus infections, boils, lacerations and swollen glands with faster healing of the soft tissues involved.

6. Relieving muscle contractions and spasms.

7. Reducing pain in MS patients while improving their perception and control, bladder, etc.

8. Enhancing the effects of physical massage by applying electrical stimulation to selected points in the area being massaged.

The present machine produces particularly beneficial effects by generating asymetrical, unipolar voltage spikes which are known to have a neuro-muscular theraputic value. The machine is fairly easy to use, especially in the automatic restart mode where a simple removal and subsequent replacement of the probe on the patient is sufficient to restart the timer and the entire stimulation procedure. Thus, it is not necessary to reset any of the front panel controls and the operator is free to devote his full attention to the patient. This device is also convenient to use in that it requires only a unipolar power source of twelve volts DC. Most important, of course, is the fact that the device provides a comfortable stimulation to the patient and that the full intensity of the stimulation pulses are increased over a 4–5 second interval, thus avoiding any jolts to the patient. Also, the machine checks for continuity before each and every stimulation pulse, thus removing the possibility that the probe has lost continuity with the patient's skin.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of applying transcutaneous electrical nerve stimulation to a patient, comprising the steps of:
   contacting a pair of probes to the patient;
   producing a continuity check clock signal and applying this signal to the probes to ascertain that the probes are in contact with the patient;
   generating stimulation pulses having a constant peak voltages and a variable current and frequency in response to an indication that continuity between the patient and probes is present;
   applying said stimulation pulses to the probes so as to stimulate the patient;
   wherein the stimulation pulses and the continuity check pulses have the same frequency, but are out of phase with each other.

2. The method according to claim 1, wherein said stimulation pulses are applied with a reduced intensity during the time that continuity is first determined.

3. A method for applying transcutaneous electrical nerve stimulation to a patient comprising the steps of:
contacting a pair of probes to the patient;
selecting one of three modes of operation, where the first mode is controlled by a duration timer, the second mode is not controlled by the timer and the third mode is controlled by the timer but which can be automatically reset after the previous time interval has expired by removing the probe from the patient and then contacting the patient again;
generating stimulation pulses of a selected frequency;
applying said stimulation pulses through said probes to the patient;
controlling the application of the pulses according to the selected mode.

4. The method according to claim 3 further comprising the step of determining when continuity between the patient and probe is acquired.

5. The method according to claim 3, wherein said stimulation pulses have a constant peak voltage and a variable current and frequency.

6. The method according to claim 3, wherein said stimulation pulses are applied with a reduced intensity during the time that continuity is first determined.

7. A method of applying transcutaneous electrical nerve stimulation to a patient, comprising the steps of:
contacting a pair of probes to the patient;
moving said probes around the patient's body in order to locate points of locally high electrical capacitance;
generating stimulation pulses of a selected frequency;
applying said stimulation pulses to said points of locally high electrical capacitance.

8. The method according to claim 7 further comprising the step of determining when continuity between the patient and probe is acquired.

9. The method according to claim 7, wherein said stimulation pulses have a constant peak voltage and a variable current and frequency.

10. The method according to claim 7, wherein said stimulation pulses are applied with a reduced intensity during the time that continuity is first determined.

11. A transcutaneous electrical nerve stimulation apparatus for applying electrical stimulation to a patient, comprising:
a pair of probes for contacting the body of the patient;
a waveform generator for producing stimulation pulses having a constant peak voltage and a variable current and frequency which is connected to the probes for applying the stimulation pulses to the patient;
a continuity check circuit connected to the probes for determining if continuity exists between the patient and the probe;
a control logic cirucit connected to said continuity check circuit and said waveform generator for preventing the generation of stimulation pulses in the waveform generator when continuity between the patient and probe is not present.

12. The apparatus according to claim 11, wherein said stimulation pulses are applied with a reduced intensity during the time that continuity is first determined.

13. A transcutaneous electrical nerve stimulation apparatus for applying electrical stimulation to a patient, comprising:
a pair of probes for contacting the body of the patient;
a waveform generator for producing stimulation pulses which is connected to the probes for applying the stimulation pulses to the patient;
a locate circuit connected to said probes for determining the local electrical capacitance of the patient's body between the probes;
a display for indicating this capacitance;
whereby the operator of the apparatus may determine appropriate locally high electrical capacitance points on the patient's body.

14. The apparatus according to claim 13 further comprising means for determining when continuity between the patient and probe is acquired.

15. The apparatus according to claim 13, wherein said stimulation pulses have a contant peak voltage and a variable current and frequency.

16. The apparatus according to claim 13, wherein said stimulation pulses have a reduced intensity during the time that continuity is first determined.

17. A transcutaneous electrical nerve stimulation apparatus for applying electrical stimulation to a patient, comprising:
a pair of probes for contacting the body of the patient;
a waveform generator for producing stimulation pulses having a constant peak voltage and a variable current and frequency which is connected to the probes for applying the stimulation pulses to the patient;
a timer control circuit connected to said waveform generator for determining when a preset duration of time has expired and for preventing the application of the stimulation pulses to the probes after the time has expired.

18. The apparatus according to claim 17 further comprising means for determining when continuity between the patient and probe is acquired.

19. The apparatus according to claim 17, wherein said stimulation pulses have a reduced intensity during the time that continuity is first determined.

20. A transcutaneous electrical nerve stimulation apparatus for applying electrical stimulation to a patient, comprising:
a pair of probes for contacting the body of the patient;
a waveform generator for producing stimulation pulses which is connected to the probes for applying the stimulation pulses to the patient;
a mode select switch for selecting one of a plurality of operating modes;
a control logic circuit connecting to said mode select switch to the waveform generator for controlling the waveform generator according to the selected mode;
a timer circuit connected to said control logic circuit for measuring a preset duration of time;
wherein said control logic operates in a first mode to allow stimulation pulses to be applied from the waveform generator to the probes during the duration of time indicated by the timer;
wherein said control logic operates in a second mode to allow the stimulation pulses to be applied from the waveform generator to the probes continuously without reference to the duration; and
wherein said control logic operates in the third mode to allow the stimulation pulses to be applied from the waveform generator to the probes during the duration and by resetting said timer to begin a new duration when the preset duration has expired, when a probe has been removed from the patient and contacted to the patient again.

21. The apparatus according to claim 20 further comprising means for determining when continuity between the patient and probe is acquired.

22. The apparatus according to claim 20, wherein said stimulation pulses have a constant peak voltage and a variable current and frequency.

23. The apparatus according to claim 20, wherein said stimulation pulses have a reduced intensity during the time that continuity is first determined.

* * * * *